United States Patent
Parkes et al.

(10) Patent No.: US 10,489,368 B1
(45) Date of Patent: Nov. 26, 2019

(54) DATAPATH GRAPH WITH UPDATE DETECTION USING FINGERPRINTS

(71) Applicant: Ascension Labs, Inc., East Palo Alto, CA (US)

(72) Inventors: Steven M. Parkes, Palo Alto, CA (US); Sean M. Knapp, Los Gatos, CA (US); Rui Yang, Sunnyvale, CA (US); Shengyang Xu, Sunnyvale, CA (US)

(73) Assignee: Ascension Labs, Inc., East Palo Alto, CA (US)

( * ) Notice: Subject to any disclaimer, the term of this patent is extended or adjusted under 35 U.S.C. 154(b) by 432 days.

(21) Appl. No.: 15/378,718

(22) Filed: Dec. 14, 2016

(51) Int. Cl.
| | | |
|---|---|---|
| *G06F 17/30* | (2006.01) | |
| *G06F 16/22* | (2019.01) | |
| *G06F 16/23* | (2019.01) | |
| *G06F 16/21* | (2019.01) | |
| *G06F 19/00* | (2018.01) | |
| *G16B 20/00* | (2019.01) | |

(52) U.S. Cl.
CPC ........ *G06F 16/2255* (2019.01); *G06F 16/217* (2019.01); *G06F 16/23* (2019.01); *G06F 16/2228* (2019.01); *G06F 19/32* (2013.01); *G16B 20/00* (2019.02)

(58) Field of Classification Search
CPC .... G06F 16/2255; G06F 16/217; G06F 16/23; G06F 16/2228; G06F 19/32; G16B 20/00
See application file for complete search history.

(56) References Cited

U.S. PATENT DOCUMENTS

| | | | | |
|---|---|---|---|---|
| 8,495,552 | B1* | 7/2013 | Cho | G06F 17/505 716/105 |
| 9,705,985 | B1* | 7/2017 | Chowdhuri | H04L 67/1097 |
| 2002/0082795 | A1* | 6/2002 | Quach | G06F 11/10 702/117 |
| 2004/0143713 | A1* | 7/2004 | Niles | G06F 11/1453 711/162 |
| 2005/0154938 | A1* | 7/2005 | McLamb | G06F 11/1438 714/17 |
| 2006/0053181 | A1* | 3/2006 | Anand | G06F 11/0715 |
| 2006/0229979 | A1* | 10/2006 | Sato | G06Q 20/10 705/39 |
| 2009/0182991 | A1* | 7/2009 | Quach | G06F 9/30189 712/222 |
| 2014/0068274 | A1* | 3/2014 | Kasatkin | G06F 21/64 713/189 |
| 2015/0207711 | A1* | 7/2015 | Le Merrer | H04L 41/5009 709/224 |
| 2016/0269175 | A1* | 9/2016 | Cammarota | G09C 1/00 |
| 2017/0109364 | A1* | 4/2017 | Hasegawa | G06F 16/1748 |

* cited by examiner

*Primary Examiner* — Jared M Bibbee
(74) *Attorney, Agent, or Firm* — Van Pelt, Yi & James LLP

(57) ABSTRACT

A current fingerprint that is a function of an operation node and an input storage node is generated. The current fingerprint is compared to a previously generated fingerprint associated with an output storage node and a task associated with performing the operation node on the input storage node is generated.

17 Claims, 11 Drawing Sheets

$F_{in}$ = f(<name of script to list logs>, quotient(<clock>,<period>))

402 — 404

Operation Node with Sub-Operations

US 10,489,368 B1

DATAPATH GRAPH WITH UPDATE DETECTION USING FINGERPRINTS

BACKGROUND OF THE INVENTION

Systems which process and/or store data can generally be divided into two types of systems: big data systems (e.g., which process and/or store terabytes or even petabytes of data) and non-big data systems (e.g., which store smaller amounts of data). Sometimes, a business or enterprise will have both types of systems. For example, a business may use big data processing and/or storage services from a first provider, as well as non-big data processing and/or storage services from another provider. New techniques which process and/or transform data from (as an example) a big data source and store the transformed data in a non-big data sink would be desirable. It would be desirable if such processing systems were robust enough to withstand underlying (sub) processes (e.g., between the source and the sink) failing and/or permitted those underlying (sub)processes to be updated.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Figure 1:
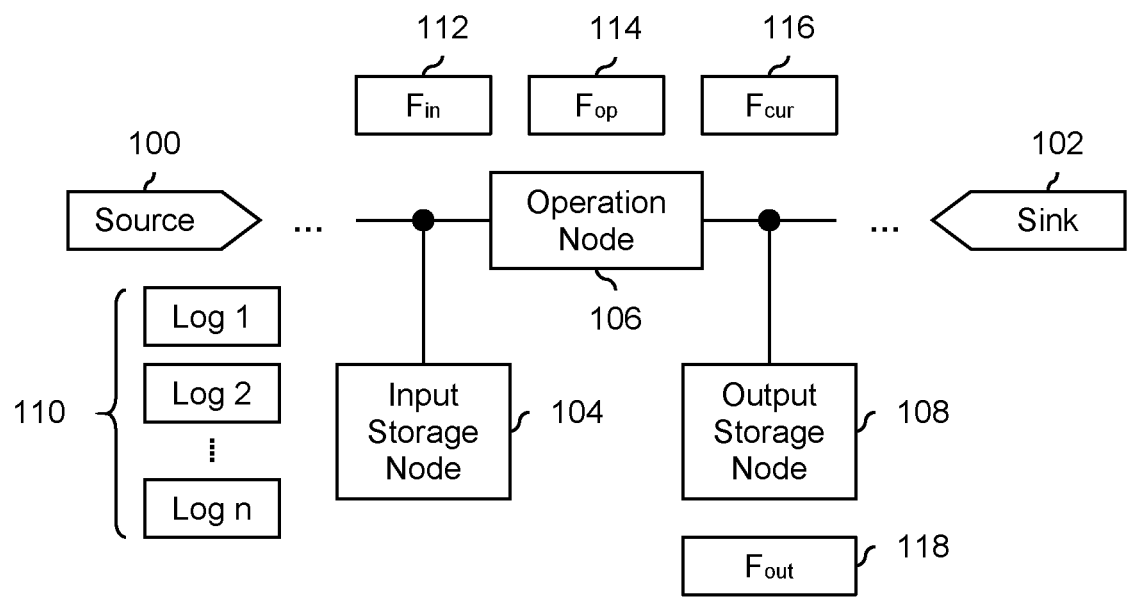
FIG. 1 is a diagram illustrating an embodiment of a datapath graph.

FIG. 1 is a diagram illustrating an embodiment of a datapath graph. Generally speaking, a datapath graph includes one or more operation nodes and one or more storage nodes. As a whole, a datapath graph transforms and/or otherwise processes data from one or more sources (e.g., source 100) and stores the transformed and/or processed data in one or more sinks (e.g., sink 102).

The overall process or transformation (e.g., from source 100 to sink 102) may be relatively complex and therefore the overall process or transformation is broken down into any number of smaller operations. Operation nodes (e.g., operation node 106) are therefore associated with some smaller operation which contributes to or is otherwise a part of the overall transformation or process. For simplicity and clarity, a simple exemplary portion of a datapath graph is shown here with an input storage node (104), operation node (106), and output storage node (108) arranged in series. However, a real-world datapath graph may include a much more complex arrangement of operation nodes and/or storage nodes (e.g., in parallel, with nodes that branch out, with nodes that merge together, etc.). To put it another way, a datapath graph may include any number of sources, sinks, operation nodes, input storage nodes, and output storage nodes. In some embodiments, a datapath graph has no loops or looping paths (e.g., for design simplicity and/or ease of implementation).

Storage nodes (e.g., input storage node 104 and output storage node 108) are used to store data which is input to and/or output from an adjacent operation node (e.g., operation node 106). An output storage node may be the input storage node for a subsequent or downstream operation node and vice versa. For example, input storage node 104 is the output storage node for some earlier operation node (not shown) and output storage node 108 is the input storage node for some subsequent operation node (not shown). In some embodiments, a storage node will be internally replicated to provide failure tolerance. Although not explicitly called out or described in examples below, this feature may be used in any implementation.

In some embodiments, an operation node includes or is associated with an SQL operation or query. In some embodiments, data which is input to an SQL operation or query must be stored in some memory or storage which can be queried or otherwise read (e.g., as opposed to directly passing the input data to the operation node from some previous operation node without intervening storage). The storage of data in an input storage node satisfies such requirements. Naturally, if an operation node does not have this requirement, then it is not a requirement to use a storage node at that juncture in the datapath graph.

In this example, a scheduler (not shown) is responsible for detecting which parts of the datapath graph are out of date and, when appropriate, initiating an update of that portion of the datapath graph. In some cases, a datapath graph becomes out of date because new data arrives or is otherwise generated by the source. In this example, the datapath graph inputs or otherwise ingests logs (110) which are generated by the source (100). For example, the source may include services or processes which read logs (e.g., which records the files or data being operated on by a user, a timestamp, a user account for which the processing is being performed, error messages, etc.). In this example, the logs are immutable or unchangeable, so once a log is created it is never subsequently modified (at least in this example). However, new logs can and do arrive at source 100. Therefore, in one example of how the datapath graph may become out of date, the data in the input storage node (104), the output storage node (108), and sink (102) becomes (e.g., globally) out of date when a new log (e.g., the $n^{th}$ log) arrives or is otherwise generated by source 100.

In another example of how a datapath graph may become out of date, some aspect of the operation associated with an operation node may change. For example, suppose operation node 106 finds the second degree polynomial that best fits the data in input storage node 104 (e.g., the operation node determines the coefficients a, b, and c for $y=ax^3+bx^2+c$). Suppose a more accurate estimation or best fit curve is desired and the operation node switches from an operation called "find_best_second_order_curve" to "find_best_third_order_curve." This change in operations would cause the data in output storage node 108 (and all subsequent or downstream data) to be (e.g., both globally and locally) out of date and the operation node would need to be rerun.

Or, suppose the operation itself did not change, but some setting or parameter to the operation (node) changed. For example, suppose there is a setting or parameter passed to operation node 106 which specifies the units associated with the input/output data (e.g., Celsius versus Fahrenheit, pounds versus kilograms, miles versus kilometers, etc.). If the setting or parameter changed from one unit to another unit (e.g., from Celsius to Fahrenheit), then the data in output storage node 108 (and all subsequent or downstream data) would be (e.g., both globally and locally) out of date and the operation node would need to be rerun.

These examples of how a datapath graph becomes out of date are able to be detected by a scheduler using (e.g., low-collision or cryptographic) hashes (sometimes referred to herein as fingerprints). As will be described in more detail below, input fingerprint 112, operation fingerprint 114, current fingerprint 116, and output fingerprint 118 are used by a scheduler to detect when an output storage node (such as output storage node 108) is (at least locally) out of date.

Before proceeding further, it may be helpful to discuss the concept of something being locally out of date versus something being globally out of date. To illustrate this, consider output storage node 108. Conceptually speaking, whether or not output storage node 108 is considered locally out of date depends upon its local environment (e.g., the state of input storage node 104 and operation node 106). So, if input storage node 104 had new or updated data which operation node 106 had not yet processed, then output storage node 108 would be considered locally out of date. In some cases, data can be streamed from previous operations (not shown), by passing storage nodes, e.g., storage node 106 in the figure. Whether a storage node is used or not is implementation and operation dependent. When a storage node is not used, fingerprints are computed recursively, e.g., instead of using a fingerprint from storage node 104, the fingerprint of the upstream operation node is used, computed as described below. As will be described in more detail below, the out of date state is reflected or captured by a change in the input fingerprint (112). Or, if the operation itself and/or some setting associated with operation node 106 changed, then output storage node 108 would be considered locally out of date. As will be described in more detail below, this is reflected or captured by a change in the operation fingerprint (114).

Output storage node 108 is considered globally out of date when there is some change in the global environment (e.g., a new log arriving at the source, some change to the operation or any of its upstream operations or settings, etc.) which affects output storage node 108. That is, whether or not output storage node 108 is considered globally out of date is evaluated in the context of its global environment (e.g., from source 100 to output storage node 108, since downstream nodes do not affect output storage node 108). So, a new log at the source would make output storage node 108 globally out of date, but output storage node 108 would not be locally out of date until the data from the new log made it to input storage node 104. The following table describes all possible global and local combinations.

TABLE 1

Example matrix of all possible local and global state combinations.

| | Output Storage Node is Globally Up to Date | Output Storage Node is Globally Out of Date |
|---|---|---|
| Output Storage Node is Locally Up to Date | Scheduler: corresponding operation node does not need to be rerun (e.g., because everything is up to date) | Scheduler: rerunning operation node now would be ineffective (e.g., because input storage node has old/out of date data) |
| Output Storage Node is Locally Out of Date | Not a possible combination | Scheduler: operation node should be rerun now (e.g., because input storage node has new/up to date data) |

The following describes the various fingerprints shown in this example and describes some examples for how they may be generated.

Input Fingerprint/Output Fingerprint

In this example, the source (100) is associated with a big data database and therefore the amount of data (i.e., content) stored in any storage node may be quite large. Instead of basing the input or output fingerprint on the data or content itself (which may be expensive to compute), the input or output fingerprint (at least in this example) depends on one or more pieces of metadata stored in or otherwise associated with the input or output storage node. For example, suppose the data stored in the input (output) storage node has some concept or sense of grouping, such as having the data stored in different tables (e.g., in a database) or different files. In one example, the input (output) fingerprint depends upon all of the names of the groups of data (e.g., stored in that storage node) and the last time each group of data was modified, such as:

$F_{in(out)} = f(\text{<name of 1st table>},\text{<last time 1st table was modified>}, \ldots,$ $\text{<name of nth table>},\text{<last time nth table was modified>})$ or $F_{in(out)} = f(\text{<name of 1st file>},\text{<last time 1st file was modified>}, \ldots,$ $\text{<name of nth file>},\text{<last time nth file was modified>})$ Thus, if a new file or table arrives, if a file or table name changes, and/or a timestamp changes, the input or output fingerprint will change. In some embodiments, instead of a file name, the name of a fragment and/or artifact is used to generate an input or output fingerprint. An artifact is made up of one or more fragments. All fragments associated with the same artifact store the same type of data (e.g., bytes, records, etc.) and a given artifact stores a particular type of data (e.g., files which are made up of bytes from the artifacts, tables which are made up of records from the artifacts, etc.). Fragments are sometimes a single file or a single table but that is not a limiting characteristic (e.g., multiple fragments could be stored in the same file (e.g., in different areas) or in the same table (e.g., with different keys)).

One benefit to using metadata as opposed to the content of the data stored in the input or output storage node to generate an input or output fingerprint is that less data needs to be considered and the time to generate the fingerprint is independent of the input data size. For example, suppose an input storage node stores a fairly large database made up of tables where (per this example) the input fingerprint depends upon the names of the tables and the timestamps of those tables. Some other technique may generate a fingerprint (e.g., associated with the input storage node) based on the content of the tables. However, because the database/tables is/are quite large, it would take longer to generate such a fingerprint compared to the example described herein (where a fingerprint is generated from the table names and timestamps).

As will be described in more detail below, in some embodiments, an output fingerprint (e.g., 118) is not updated until a scheduler is assured that all processing (e.g., associated with the operation node which writes to that output storage node) has completely and properly finished. For example, a scheduler may not update output fingerprint 118 until the scheduler is sure that all operations (e.g., associated with rerunning operation node 106) have completely and properly finished. This may prevent the data in output storage node 108 from being in some hybrid state where the data is an improper combination of old data (e.g., from a previous execution of the operation node) and new data (e.g., from the current, but failed, execution of the operation node) and prevent such improper combinations of data from being propagated downstream. This may also prevent improper output fingerprint values from being propagated downstream prematurely.

In some embodiments described below, data is stored or arranged in artifacts (e.g., in an input or output storage node) and each artifact is made up of one or more fragments. As will be described in more detail below, an input or output fingerprint may depend upon artifact-level fingerprints and/or fragment-level fingerprints.

Generally speaking, the input fingerprint is generated in a manner which is conservative with respect to detecting a change to data stored in the input node. That is, in this example, a false positive at the input fingerprint (e.g., where the input fingerprint changes but the data in the input storage node has not changed in a manner which requires or otherwise necessitates rerunning of the operation node) is acceptable, but false negatives (e.g., where the input fingerprint has not changed but the data in the input storage node has changed in a manner which requires or otherwise necessitates rerunning of the operation node) are not acceptable.

An input and/or output fingerprint may be stored in a variety of locations (at least in those embodiments where they are stored). For example, they may be stored in some metadata database (e.g., with other fingerprints).

Operation Fingerprint

As described above, a change to the operation name (e.g., switching from an operation called "find_best_second_order_curve" to a different operation called "find_best_third_order_curve") or a change to some setting or parameter used by the operation may necessitate the rerunning of an operation node. To capture this (i.e., so that the operation fingerprint changes whenever some change to the operation itself or an operation setting triggers rerunning of the operation node), the operation fingerprint in this example is a function of the name of the operation and one or more settings or parameters selected from all possible settings or parameters. For example:

$F_{op} = f(\text{<name of operation>}, \text{<1st selected setting>}, \ldots, \text{<nth selected setting>})$ For example, not all settings may necessitate the rerunning of the operation node (i.e., not all settings may cause the output storage node to become out of date) and those settings are not used to generate the operation fingerprint.

Naturally, what inputs or pieces of information are used to generate the operation fingerprint are implementation dependent. Different fields or pieces of metadata may be available and/or what pieces of metadata are informative (e.g., as to whether to rerun the operation node) depend upon the particular implementation. The following table includes inputs which (in various embodiments) are useful in detecting when an operation changes and/or should be rerun. Naturally, this list is merely exemplary and is not intended to be limiting.

TABLE 2

Example inputs for operation fingerprint

| | |
|---|---|
| Operation name | For example, "find_best_second_order_curve" or "find_best_third_order_curve" |
| (Selected) setting or parameter | For example, a setting which: specifies a unit associated with the input/output data (see examples above); specifies a localization format associated with the input/output data (e.g., Asian naming format (i.e., last name first), European date format (i.e., day, month, year), etc.); specifies a degree of precision or specificity (e.g., round to nearest tenths, to nearest hundredths, etc.); specifies a field to input or otherwise process (e.g., username, acct no, |

TABLE 2-continued

Example inputs for operation fingerprint

| | |
|---|---|
| Operation name | For example, "find_best_second_order_curve" or "find_best_third_order_curve" |
| | org_unit, etc.); and/or specifies some threshold (e.g., to filter input data on) or number of groups (e.g., to sort the data into). |
| Path at which operation is located | For example, to be safe, the operation node may be rerun if the path to the operation (e.g., where the executable is stored) changes |
| Operation version number | For example, in some cases, the operation name and path may not change, but if the version number changes, the operation node is rerun to be safe |

One benefit to the example inputs from the table above is that they are relatively small and generating an operation fingerprint from them is relatively fast. For example, suppose some other technique generates a fingerprint directly from the executable code associated with some operation node. The executable code may have hundreds or even thousands of lines of code for a complex operation. The fingerprint generator would have to ingest all of those lines of code, which is much more data than the inputs from the table above.

As with the input fingerprint, the operation fingerprint is generated in a manner which is conservative with respect to detecting a change to the operation node. A false positive at the operation fingerprint (e.g., where the operation fingerprint changes but the operation node does not need to be rerun) is acceptable but false negatives (e.g., where the operation fingerprint has not changed but the operation node does need to be rerun) are not acceptable.

In some embodiments, an operation fingerprint (e.g., 114) is stored on an operation node (e.g., 106).

Current Fingerprint

The current fingerprint (116) depends upon the input fingerprint (112) and the operation fingerprint (114). That is:

$$F_{cur}=f(F_{in},F_{op})$$

For example, the input fingerprint and operation fingerprint may be combined using a hash. In some embodiments, a weaker process such as an exclusive OR (XOR) is used but the chance of collisions increases which is not desirable.

Generally speaking, a scheduler will know that output storage node 108 is locally out of date and should be rerun (e.g., now) if the current fingerprint (116) and the output fingerprint (118) do not match. As described above, this could be because the operation itself or some setting associated with operation node 106 changed (e.g., which would be captured or otherwise reflected by a change in operation fingerprint 114) or due to some new log arriving at source 100 or some change to an upstream operation node (e.g., which would be captured or otherwise reflected by a change in input fingerprint 112). In some embodiments, when current fingerprint 116 and output fingerprint 118 do not match, the scheduler generates a task to rerun the operation node (e.g., where the task is actually performed by some worker).

If the current fingerprint (116) and the output fingerprint (118) do match, then output storage node 108 is locally up to date and the scheduler will not rerun operation node 106. As described above, the output storage node could be globally out of date (e.g., because of some new log at source 100, where the information from the new log has not yet propagated itself to input storage node 104). If desired, the scheduler may determine what portions of the datapath graph are globally out of date. For example, fingerprints may be propagated from the source to the sink (e.g., without waiting for operation nodes in the datapath graph to be rerun and/or without writing over corresponding fingerprints which need to be preserved until upstream operation nodes have had time to complete) and current fingerprints and output fingerprints can be compared as described above. In one example application, the scheduler does this so a user knows if the sink is globally up to date.

In some embodiments, there are various owners and/or providers of the storage devices shown here (e.g., source 100, input storage node 104, output storage node 108, and/or sink 102). For example, source 100 may be a cloud-based, big data storage service provided by Amazon. Sink 102 may be a SQL (i.e., non-big data) database provided by Oracle (e.g., cloud-based or physically stored on the customer/user's system). The owner of the content or data on source 100 and sink 102 may be some business which wants to move (e.g., without or without some transformation or processing of) its content or data from source 100 to sink 102. For example, the business may have a service agreement with Amazon associated with source 100 and may have a similar service agreement with Oracle associated with sink 102 so that it can store, manipulate, and/or access its content on source 100 and sink 102, respectively. In some embodiments, input storage node 104 and output storage node 108 and the data thereon are owned by some datapath platform provider (e.g., Ascension Labs). The storage itself for input storage node 104 and output storage node 108 may be obtained from a storage provider (e.g., Amazon) but may be leased and managed by the datapath platform provider (e.g., Ascension Labs).

The following figure describes (e.g., in a more general manner than above) a process for updating at least part of a datapath graph fingerprints, which may include using a low collision hash.

Figure 2:
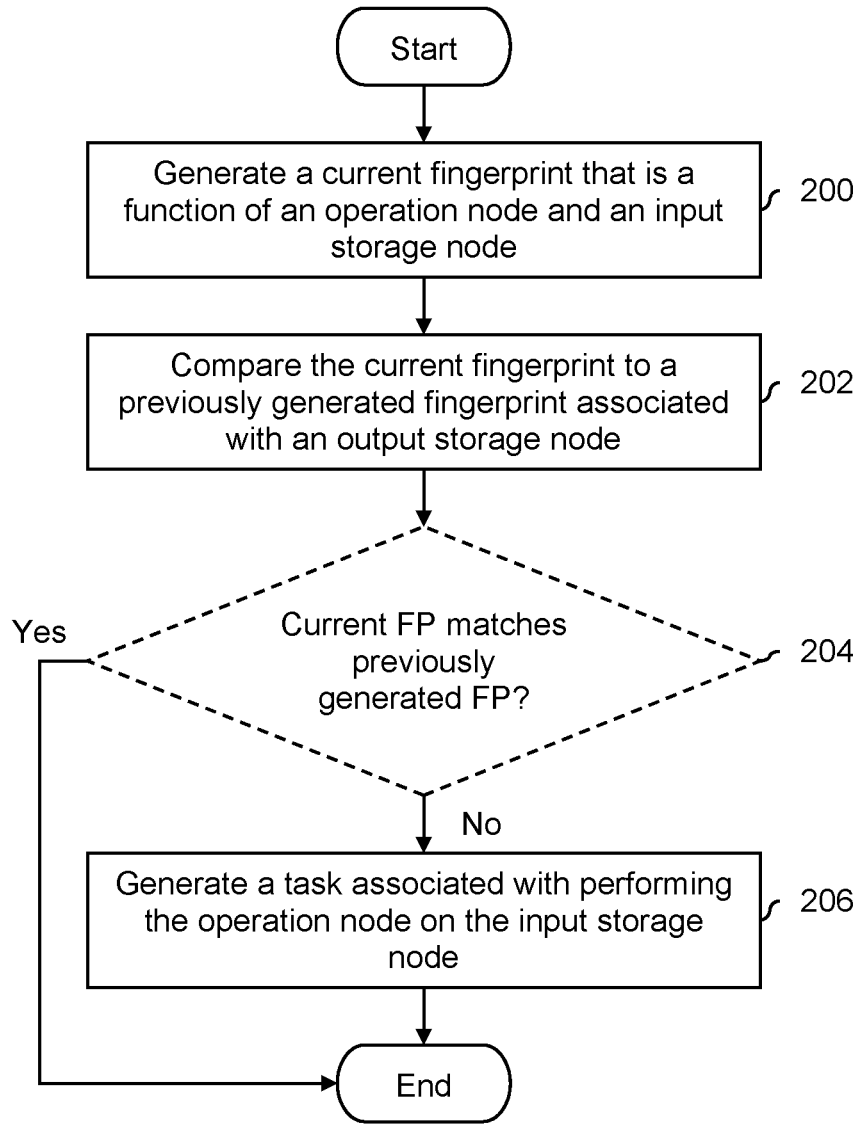
FIG. 2 is a flowchart illustrating an embodiment of a process to update at least part of a datapath graph using hashes.

FIG. 2 is a flowchart illustrating an embodiment of a process to update at least part of a datapath graph using hashes. In some embodiments, the process is performed by a scheduler.

At 200, a current fingerprint that is a function of an operation node and an input storage node is generated. For example, in FIG. 1, input fingerprint 112 depends upon and/or is representative of the data in input storage node 104 (e.g., so that it changes when the data therein changes). Similarly, operation fingerprint 114 depends upon and/or is representative of the state of operation node 106 (e.g., so that it changes when there is some change to the operation itself or a setting input by the operation). As described above, in the example of FIG. 1, current fingerprint 116 depends upon input fingerprint 112 and operation fingerprint 114. In some embodiments, not all of the fingerprints are saved or otherwise stored by the system. For example, input fingerprints and/or operation fingerprints may be generated when or as needed by the system (e.g., at step 200). Similarly, a datapath graph may not necessarily include all of the nodes shown in FIG. 1. FIG. 1 shows input storage nodes, output storage nodes, and operation nodes because they are conceptually useful in explaining the technique, but in an actual implementation some or all of the nodes are not actually required (e.g., there is no input storage node). In some embodiments, a current fingerprint is generated at step 102 by using a low collision hash (e.g., Murmur, cryptographic hashes, etc.) to combine an input fingerprint and an operation fingerprint.

At 202, the current fingerprint is compared to a previously generated fingerprint associated with an output storage node. For example, in FIG. 1, output fingerprint 118 is an example of a previously generated fingerprint. In FIG. 1, output fingerprint 118 depends upon and/or is representative of the state of output storage node 108 (e.g., so that it changes when the data may have changed. Because hashes are based on metadata, in some cases, a hash may have changed when the underlying data has not. In some embodiments, this may cause duplicate computation but will always eventually compute the correct, consistent result).

At 204, it is determined if the current fingerprint matches the previously generated fingerprint. If the current fingerprint does not match the previously generated fingerprint, a task associated with performing the operation node on the input storage node is generated at 206. As described above, in this scenario, the output storage node is locally out of date and the operation node is rerun in order to update the data stored in the output storage node. In some cases, the task generated at step 206 is actually performed by a worker (e.g., as opposed to the scheduler). Although step 206 recites a single task, in some embodiments a plurality of tasks are generated. To put it another way, step 206 in some embodiments includes generating a set of one or more tasks.

If the current fingerprint is determined to match the previously generated fingerprint at 204, the process of FIG. 2 ends. As described above, in this scenario, the output storage node is locally up to date but may or may not be globally out of date. If the output storage node is locally up to date but globally out of date, it would do no good to rerun the operation node at least at this time because the new data (or, more generally, the change) has not yet propagated to the input storage node.

In one example of how the process of FIG. 2 is used or otherwise applied, the scheduler repeatedly performs the process of FIG. 2 at some specified frequency or interval (e.g., every five seconds, every minute, etc.) for every output storage node.

It may be useful at this point to describe the datapath graph in the context of a specific application. The following figure illustrates an example of a datapath graph in a medical research application.

Figure 3:
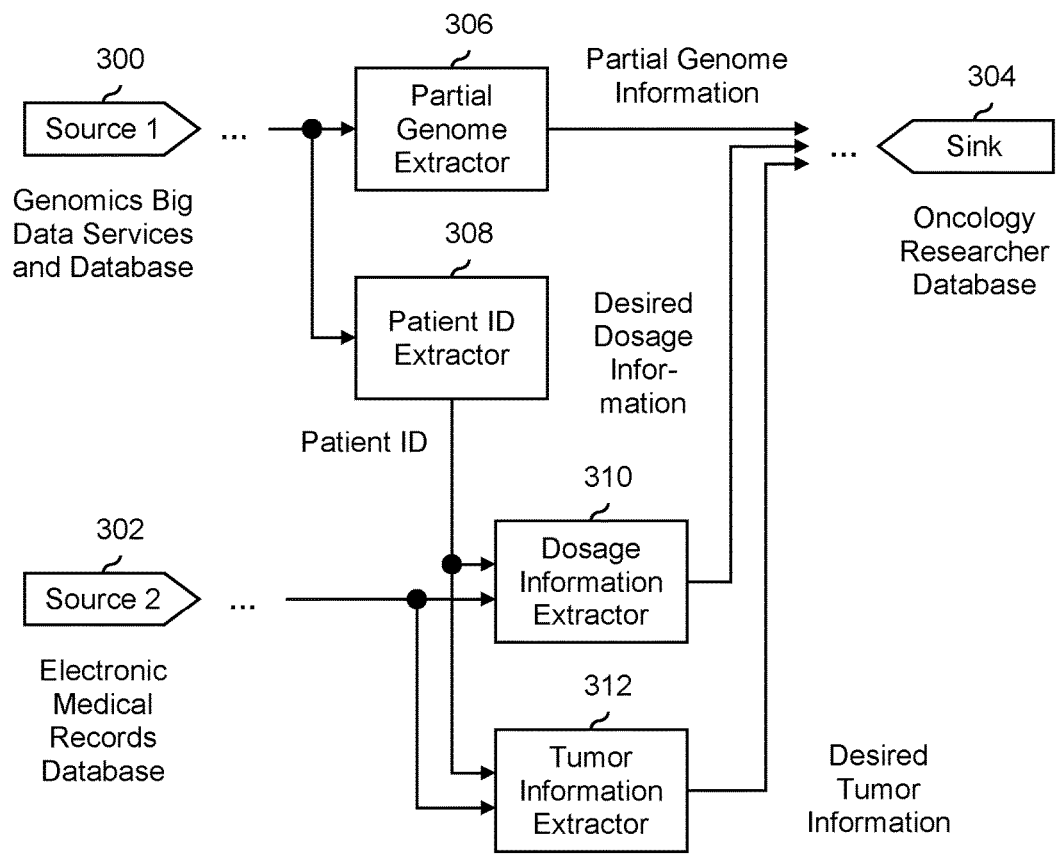
FIG. 3 is a diagram illustrating an embodiment of a datapath graph used in an oncological research application.

FIG. 3 is a diagram illustrating an embodiment of a datapath graph used in an oncological research application. To preserve the readability of this figure, input and output storage nodes associated with the exemplary operation nodes are not shown. Furthermore, a real-world datapath graph may include additional operation nodes not shown here, including (as an example) operation nodes associated with reading data from the source(s) and/or writing data to the sink(s). Again, to preserve the readability of this figure, such operation nodes are not shown here.

In this example, a cancer researcher is investigating the use of a drug to treat a solid tumor. The cancer researcher wants to know if the drug being investigated is particularly effective for patients with certain DNA sequences and (if so) what that particular DNA sequence is and where that DNA sequence is located. The information the researcher needs to answer this question is located in multiple sources and those sources store other information which is not of interest to the researcher. Both sources are quite large and therefore reading directly from the sources is undesirable because it is slow and in the case of the first source (300) may incur access-related fees. Therefore, the purpose (generally speaking) of the exemplary datapath graph shown here is to extract some specified and/or desired information from the first source (300) and second source (302) and put that specified and/or desired information in the sink (304).

In this example, the first source (300) provides genome-related big data services and storage. The first source (300) stores the entire genome sequence for patients in the trial and the exemplary datapath graph writes some specified portion of the genome sequence to the sink (304). As an example, the first source may be Amazon's Simple Storage Service (S3) which is a cloud-based storage service which provides some free storage, some free number of get requests, and some free number of put requests, beyond which fees are charged. Since get requests after the free threshold incur a fee, unnecessary reads from this source are undesirable.

Operation node 306 (i.e., partial genome extractor) extracts the specified or desired part of the genome sequence for each patient in the trial. For example, partial genome extractor 306 has one or more parameters or settings which the research can use to specify the portion of the complete genome sequence to extract and write to the sink (e.g., "start_location" and "end_location" to specify the location(s) to extract).

To test the drug, different patients are given different dosages at different intervals and the response of the tumor is observed (e.g., shrink, grow, stay the same size). In this example, the second source (302) is an electronic medical records database which includes drug dosage information (e.g., dosage amounts and dates on which the drug was administered to the patient), imaging information (e.g., tumor size and image date), doctor's notes/orders, laboratory and/or imaging results, etc. In various embodiments, the second source may comprise a big data database (e.g., on the order of petabytes) or a non-big data database depending upon the size of the hospital or medical practice.

Since the electronic medical records database contains records for many patients, the patient ID for a given patient (e.g., corresponding to the partial genome information output by operation node 306) is obtained so that the corresponding dosage information and tumor information can be obtained from second source 302 (i.e., the electronic medical records database). Operation node 308 (i.e., patient ID extractor) outputs the patient ID corresponding to the partial genome information output by operation node 306. Note, for example, that partial genome extractor 306 and patient ID extractor 308 have the same input so that they can output corresponding values.

The patient ID is passed from patient ID extractor 308 to operation node 310 (i.e., dosage information extractor) and operation node 312 (i.e., tumor information extractor). In this example, dosage information extractor 310 is able to extract dosage information for a variety of drugs and therefore one of the parameters or settings for dosage information extractor 310 is "drug_name." With the patient ID and the drug name specified, dosage information extractor 310 then obtains the desired dosage information from the second source (e.g., the dosage amounts and dates on which the drug was administered to the patient) and writes it to sink 304.

In this example, operation node 312 has parameters or settings used to specify the fields in the electronic medical records from which the size of the tumor and the date of that measurement are obtained (e.g., "tumor_size" and "image_date"). For example, different electronic medical records databases may store this information in fields with different names. Tumor information extractor 312 then obtains the desired tumor information (e.g., the tumor size and the date on which the size of the tumor was measured) and writes it to sink 304.

If the first source (300) gets new genome related information (not shown), for example, in the form of one or more new logs, the input fingerprint (not shown) at the input to partial genome extractor 306 and patient ID extractor 308 will cause both of those operation nodes to be rerun so that their output storage nodes (not shown) can be updated. An example of how this is detected is described in more detail below. Similarly, if the second source (302) gets new dosage or tumor information, the input fingerprint (not shown) at the input to dosage information extractor 310 and tumor information extractor 312 will cause both of those operation nodes to be rerun so that their output storage nodes (not shown) can be updated.

A change at an operation node can also cause that operation node to be rerun. For example, suppose that the researcher wants to examine a different part of the genome sequence and adjusts the "start_location" and/or "end_location" parameters accordingly. In this example, the operation fingerprint (not shown) associated with partial genome extractor 306 depends upon the name of the operation (e.g., "partial genome extractor.exe") and the parameters "start_location" and "end_location." Since one or both of the location parameters have changed, the operation fingerprint will change, which will cause the operation node to be rerun so that its output storage node (not shown) can be updated.

The operations described here are merely exemplary and are not intended to be limiting. For example, although the datapath graph shown here is fairly simple (in that the analysis of the data is done at or on sink 304), in some embodiments, a datapath graph is used to perform relatively complex operations. For example, a datapath graph may be configured so that the analysis is done within or by the datapath graph (e.g., as opposed to doing the analysis at or on sink 304).

In some embodiments, a scheduler is not notified about new logs at a source. To use microcontroller terminology, the existence of new logs in such sources is detected by polling (i.e., there is no interrupt). Or, to use push versus pull terminology, the logs must be pulled from the source; (new) logs are not pushed from the source to the scheduler. The following figure describes one embodiment which uses fingerprints (which may include cryptographic hashes) to detect the existence of a new log at a source while avoiding excessive resource consumption.

Figure 4:
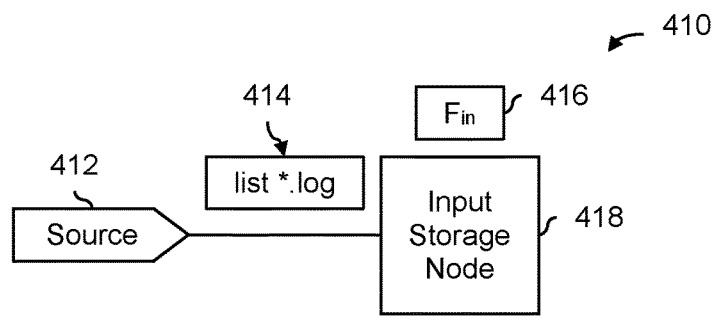
FIG. 4 is a diagram illustrating an embodiment of an input fingerprint used to detect new logs at a source.
Figure 4:
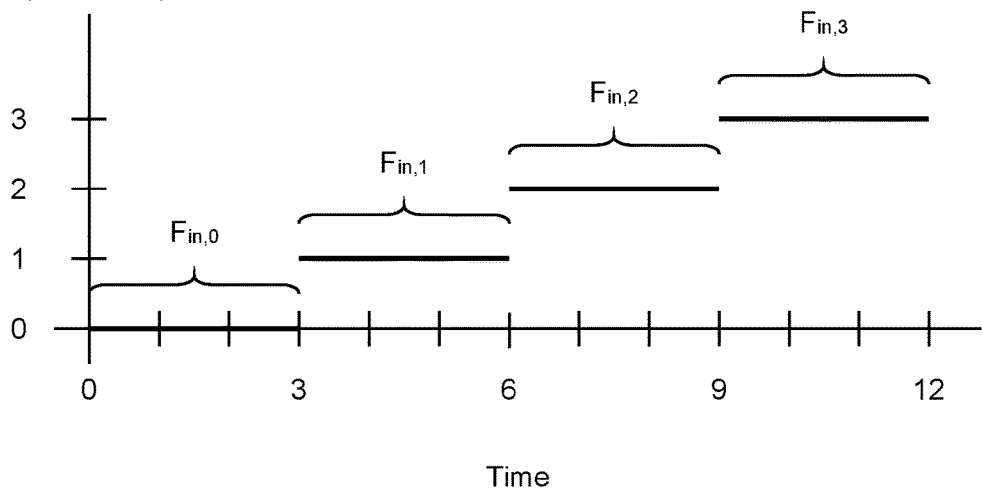

FIG. 4 is a diagram illustrating an embodiment of an input fingerprint used to detect new logs at a source. Diagram 400 shows how the exemplary fingerprint is generated. In this example, the input fingerprint depends upon two things: (1) the name of the script (402) used to list or otherwise obtain the names of logs at the source (e.g., which does not necessarily return the contents of those logs) and (2) the output of a quotient function which inputs a (e.g., free running) clock and some set or specified period (404). As will be described in more detail below, the value that the period is set to controls the frequency with which the scheduler checks the source for new logs.

In this particular example where the input fingerprint is associated with or directly comes from the source, the input fingerprint is compared against a previous version of itself to detect when to rerun a script to list logs at a source. That is, if the input fingerprint changes values, then the script is rerun.

Diagram 410 shows how the first input (i.e., the name of the script (402)) may cause the input fingerprint (416) to change and trigger a rerun of the script. In this example, script 414 (i.e., list *.log) is used to list or otherwise read all logs at source 412. In this example, the name of the script (i.e., the string "list *.log") would be used as input 402 in diagram 400. For example, if the name of the script changed (e.g., because a new script is being used to list or otherwise read all logs at source 412), then the input fingerprint (416) would change and the new script would be run (e.g., in case the new script yields a new or different result from the old script) so that input storage node 418 can be updated.

Diagram 420 shows how the second input (i.e., the quotient function (404)) may cause the input fingerprint (416) to change and trigger a rerun of the script. In this example, the period is set to 3. The x-axis in this example shows the time (e.g., associated with the free running clock) and the y-axis shows the value produced by the quotient function when the period is set to 3. For times 0-3, the quotient function returns a value of 0; for times 3-6, the quotient function returns a value of 1; for times 6-9, the quotient function returns a value of 2; for times 9-12, the quotient function returns a value of 3; and so on. When the value generated by the quotient function changes, the corresponding fingerprint changes. Therefore, at time 3 the input fingerprint changes from $F_{in,0}$ to $F_{in,1}$, at time 6 the input fingerprint changes from $F_{in,1}$ to $F_{in,2}$, at time 9 the input fingerprint changes from $F_{in,2}$ to $F_{in,3}$, and so on (e.g., assuming the name of the script stays the same during this time). In other words, whatever value the period is set to (e.g., in the quotient function), the fingerprint will change with that periodicity and the script will be rerun with that periodicity.

One benefit to this technique is that it can be tuned to check a source for new logs without constantly and/or excessively checking for new logs. For example, constantly rerunning script 414 would consume a significant amount of processing resources. Also, as described above, some sources have a limit on the number of get requests (i.e., read or list commands or instructions directed to the source). Constantly checking such sources for new logs would become very expensive since the free threshold would quickly be reached.

Another benefit is that this mechanism weaves polling into the overall graph computation via the fingerprint mechanism and makes the difference between these cases and other cases local only. That is, other code doesn't care that a computation needs to rerun because of polling or if it has to be rerun because inputs changed. This results in a better design and/or makes the other code easier to write.

In some embodiments, there are multiple sources. In some such embodiments, the respective input fingerprints may have different periods (e.g., so that the sources are checked at different frequencies for new logs). Naturally, this may depend upon the nature of the sources and/or the application.

As described above, in some embodiments an operation node includes sub-operations (e.g., with no storage inside the operation node). The following figure describes one such example.

Figure 5:
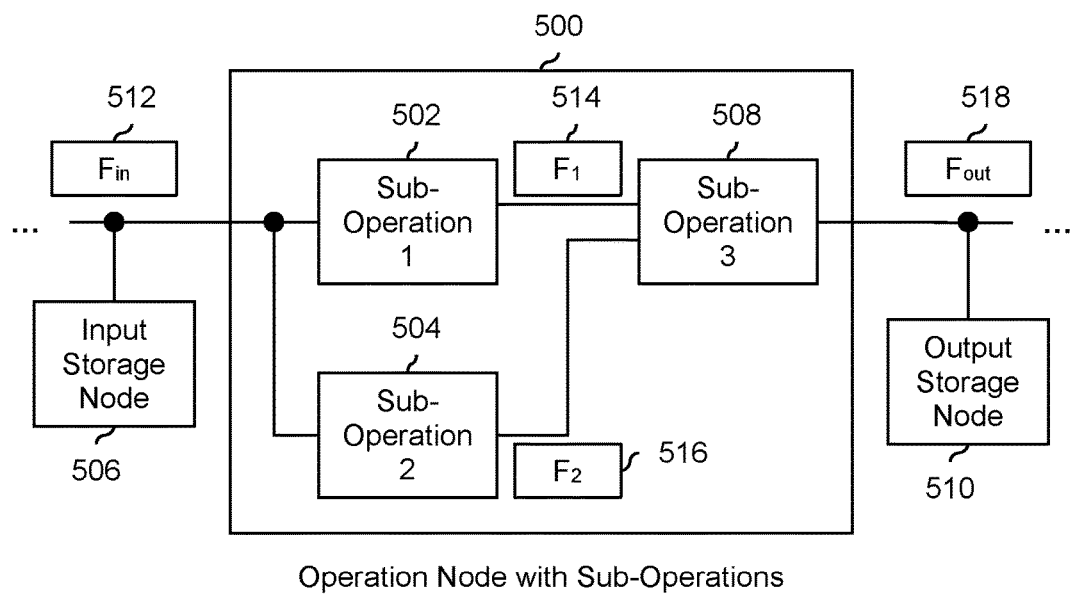
FIG. 5 is a diagram illustrating an embodiment of an operation node with sub-operations.

FIG. 5 is a diagram illustrating an embodiment of an operation node with sub-operations. For example, operation node 106 in FIG. 1 may be implemented as shown in some embodiments. In this example, operation node 500 includes three sub-operations. The first and second sub-operations (502 and 504) are in parallel at the input of operation node 500. In that position, first and second sub-operations have (e.g., direct) access to input storage node 506 and (as described above) this permits them to be implemented using SQL queries or other processes which may require their inputs to be stored in some sort of storage.

The outputs of first and second sub-operations are passed to the third sub-operation (508). It is noted that there is no storage (node) at that juncture and so the outputs of the first and second sub-operations are passed (e.g., directly) to the third sub-operation. Therefore, SQL queries or other processes which require their inputs to be stored in some sort of storage cannot be used to implement the third sub-operation. The output of the third sub-operation is stored in output storage node 510.

As before, fingerprints are used by the scheduler to determine when to rerun a particular (sub-)operation. For example, new data in input storage node 506 will cause input fingerprint 512 to change. This change in the value of input fingerprint 512 will cause the first and second sub-operations (502 and 504) to be rerun. New data at the outputs of the first and second sub-operations will cause the values of fingerprints $F_1$ (514) and $F_2$ (516) to change, respectively. Either one of those fingerprints changing will cause the third sub-operation to be rerun. New data at output storage node 510 (e.g., generated by the third sub-operation) will cause the output fingerprint (518) to change. This will cause downstream operation node(s), not shown, to be re-run.

One benefit to an operation node implemented as shown is that the amount of storage required is reduced. As described above, storage for storage nodes may be obtained from a storage provider for a fee. Since operation node 500 has no storage nodes, less storage needs to be obtained which keeps costs down and frees up processing and/or I/O resources. In some embodiments, sub-operations in an operational node are limited to simple and/or robust operations or processes where there is no anticipated need for post-processing debugging or auditing. For example, there may be a high cost and low benefit to storing input/output data for relatively simple mathematical operations such as add and subtract and storage nodes may be eliminated at such points in the datapath graph.

In some embodiments, data (e.g., in an input or output storage node) is stored in one or more artifacts where each artifact includes one or more fragments. As will be described in more detail below, this may help to reduce the amount of work which needs to be performed in certain cases.

Figure 6:
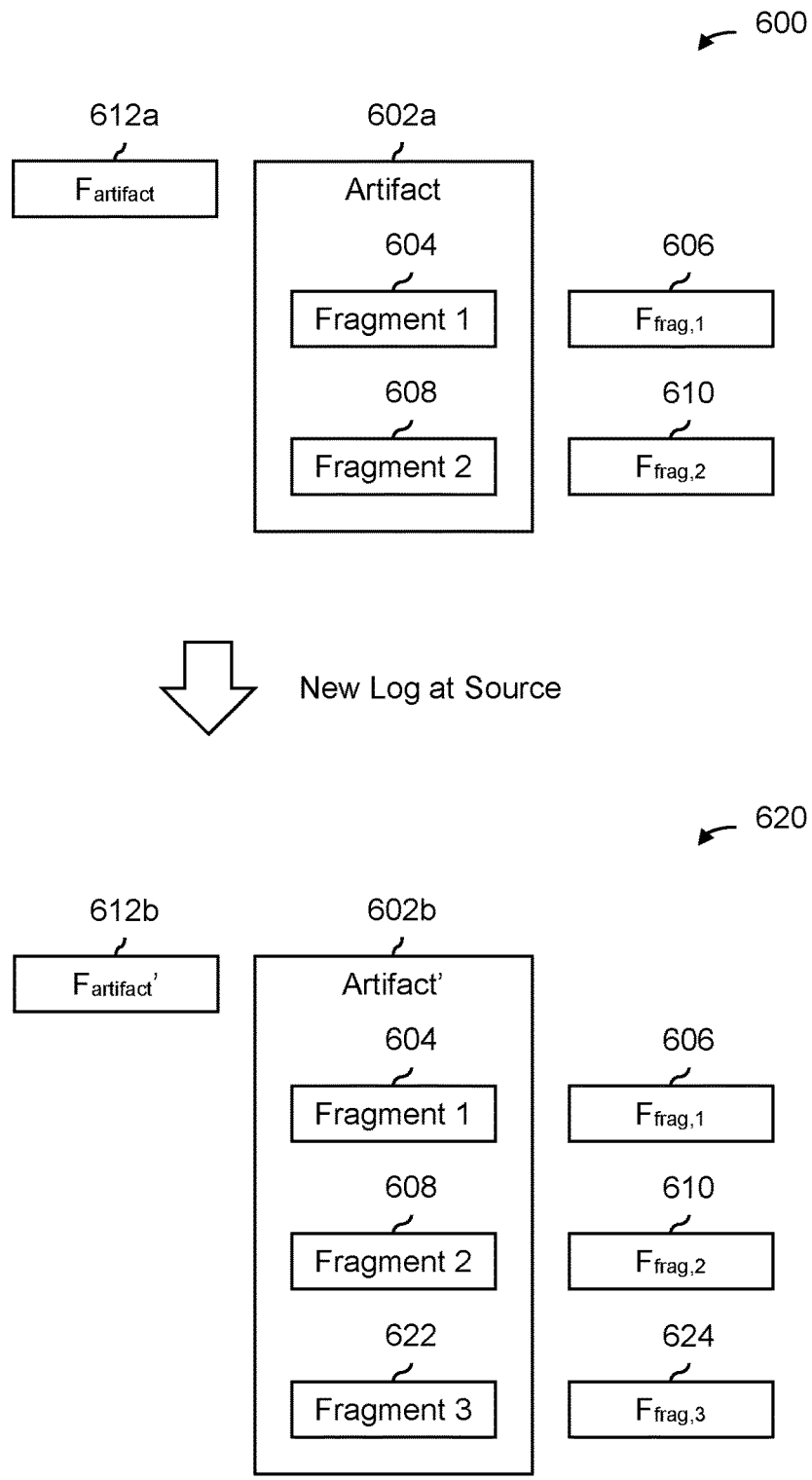
FIG. 6 is a diagram illustrating an embodiment of an artifact with a new fragment generated by the arrival of a new log at a source.

FIG. 6 is a diagram illustrating an embodiment of an artifact with a new fragment generated by the arrival of a new log at a source. In the example shown, diagram 600 shows an artifact (602*a*) and its (e.g., component) fragments (604 and 608) at a first point in time. In some embodiments, the artifact and associated fragments are stored in some storage node (e.g., an input/output storage node, not shown) where one or more operations (e.g., stored on or otherwise associated with a preceding operation node, not shown) generate the artifact and fragments.

Each of the fragments has a corresponding fragment fingerprint which is a function of the fragment. For fragments associated with sources, the fingerprints generally depend on the metadata of the input data (e.g., file names, modified times, etc.). In the case of downstream fragments, they depend on the fingerprint of the operation and the input fragment fingerprints.

The artifact fingerprint (612*a*) depends upon the value of all of the fragments included in that artifact (e.g., fragments 604 and 608 in the case of diagram 600). Another way of describing this relationship is to say that the artifact fingerprint is a function of all of the fragment fingerprints associated with that artifact (e.g., $F_{artifact}=f(F_{frag,1},F_{frag,2})$ in the case of diagram 600). For example, all of the fragment fingerprints may be combined using a low collision hash (e.g., Murmur, a cryptographic hash, etc.) to obtain the artifact fingerprint.

In this particular example, the operation which generates the exemplary artifact and fragments is an operation which generates a new fragment and does not change the old fragments. For example, suppose that each log at a source is associated with a single session of a single user with a music streaming service (e.g., once the user logs off or ends the session in some manner, a log of the user's interactions with the streaming service is generated at the source). Suppose that the operation which generates the artifact and fragments shown is associated with extracting song information from the logs so that royalties can be paid to the appropriate parties. So, every time there is a new log at the source, a new fragment is generated in the artifact and none of the older fragments are changed by the operation which generated the fragments. (Note that this is merely an example and does not hold true for all cases. Some operations require all input fragments to be reread and will generate a completely new set of fragments. It's function of/depends on the actual operation being implemented and there are unlimited number of operations that can be implemented.)

Diagram 620 shows the artifact and fragments after a new log arrives at the source and the operation has updated the fragments. As described above, the first and second fragments (604 and 608) will not change, so the first and second fragment fingerprints (606 and 610) will not change. However, in response to the new log, the operation generates a third fragment (622) which has a corresponding third fragment fingerprint (624). The third fragment also causes the artifact fingerprint to change. For example, while the old artifact fingerprint (612*a*) is $F_{artifact}=f(F_{frag,1},F_{frag,2})$, the new artifact fingerprint (612*b*) is $F_{artifact}=f(F_{frag,1},F_{frag,2},F_{frag,3})$.

The following figure shows an example of how fragment fingerprints may be used to efficiently update a locally out of date output storage node in this scenario.

Figure 7:
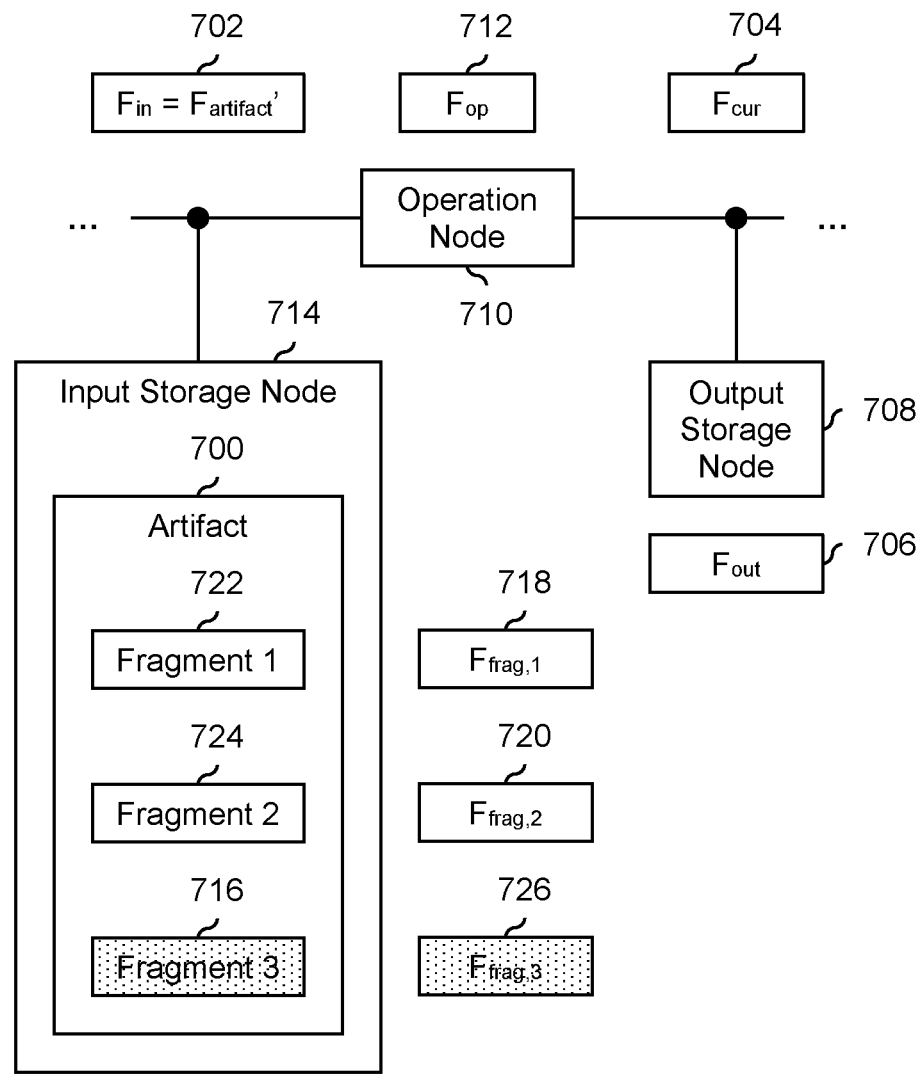
FIG. 7 is a diagram illustrating an embodiment of an artifact with a new fragment in an input storage node.

FIG. 7 is a diagram illustrating an embodiment of an artifact with a new fragment in an input storage node. In this example, the new artifact fingerprint associated with artifact 700 is used as the input fingerprint (702). Since the artifact/input fingerprint has changed, the current fingerprint (704) changes and will no longer match the output fingerprint (706). This signals to the scheduler that output storage node 708 is locally out of date and that the operation associated with operation node 710 needs to be rerun. (In this example, the operation fingerprint (712) stays the same.)

Instead of performing the operation on all of the data in input storage node 714, the operation is selectively run only on the third fragment (716), because in this example the operation generates one fragment for each input fragment. For example, the scheduler will have seen the first and second fragment fingerprints (718 and 720) before (e.g., those fingerprints do not change between diagram 600 and 620 in FIG. 6). Therefore, the scheduler will know that the operation does not need to be run for the first and second fragments (722 and 724). However, the scheduler will not have seen the third fragment fingerprint (726) before, and so the scheduler generates a task associated with performing the operation on the third fragment (716). This eliminates the unnecessary rerunning of the operation on the first and second fragments. (In some other cases, unlike the one described above, an operation does not generate one fragment for each input fragment. Some operations take multiple input fragments and generate a single output fragment. In that case, it may be necessary to run the operation against all data again.)

It is noted that this technique of using fragment fingerprints to more efficiently determine what fragments to run an operation on may be used throughout a datapath graph, even fairly early on when the logs have just been read or otherwise obtained from the source. For example, in FIG. 4, any logs in input storage node 418 (e.g., not shown in FIG. 4 but which would result from script 414) are arranged or organized as shown in FIG. 6 and/or FIG. 7. If the artifact fingerprint (e.g., input fingerprint 416 in FIG. 4) changes, the fragment fingerprints may be used to determine which fragments/logs are new so that the operation can be run only for those new fragments/logs. This may permit (e.g., even from relatively early points in a datapath graph) the efficient use of processing resources.

Artifact and fragment fingerprints may be stored in a variety of locations. In some embodiments, artifact and fragment fingerprints are stored in a metadata database. In some embodiments, the metadata database is also used to store other fingerprints which the system decides to store.

The following figure more formally describes this process of using artifact fingerprints and fragment fingerprints to more efficiently perform operations (e.g., only on those fragments which need it).

Figure 8:
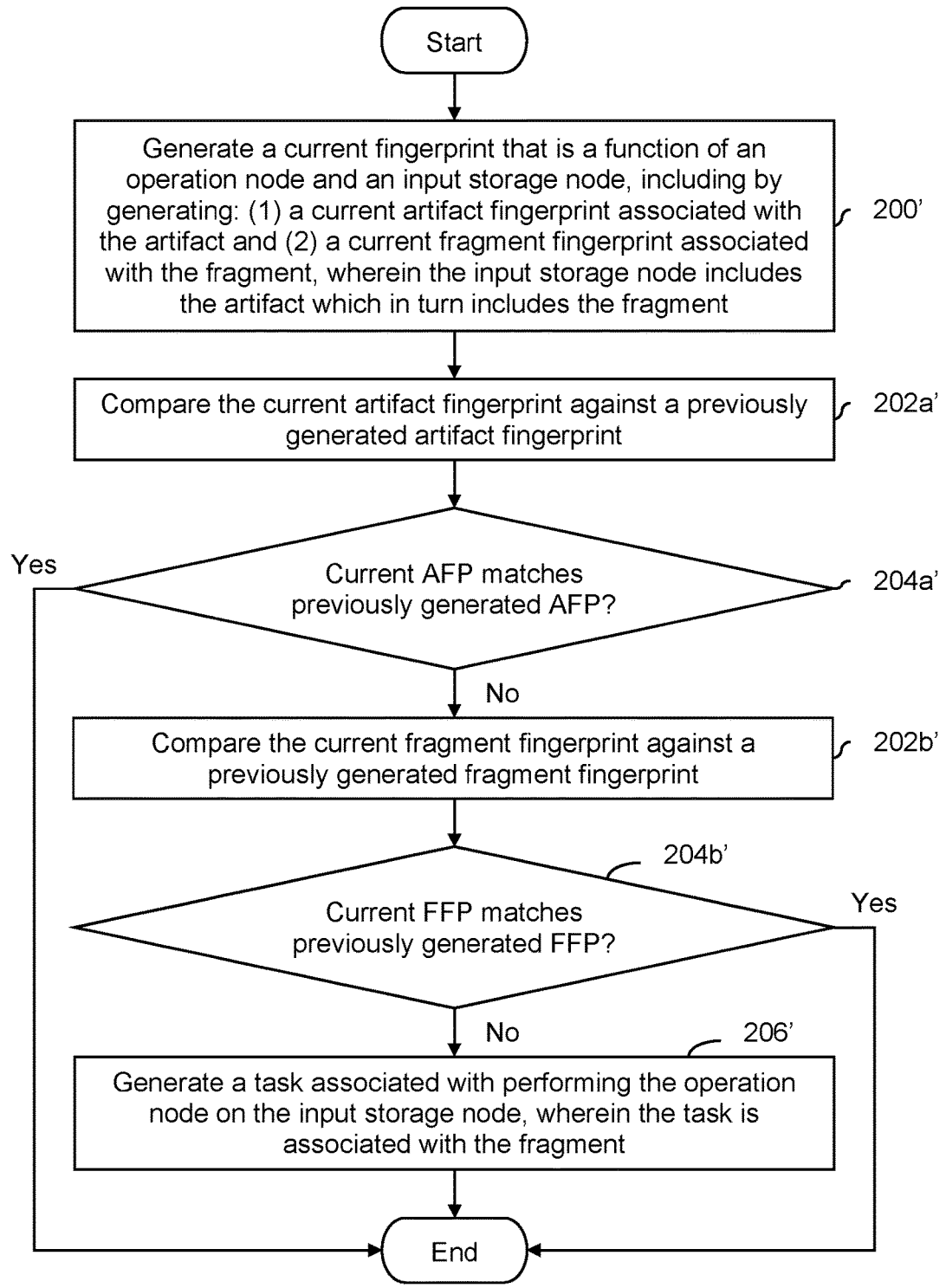
FIG. 8 is a flowchart illustrating an embodiment of a process to update at least part of a datapath graph using artifact fingerprints and fragment fingerprints.

FIG. 8 is a flowchart illustrating an embodiment of a process to update at least part of a datapath graph using artifact fingerprints and fragment fingerprints. FIG. 8 is similar to FIG. 2 and similar reference numbers are used to show similar steps. To preserve the readability of the flowchart, steps 202b', 204b', and 206' are shown only for a single fragment in this example. As described above, those steps may be repeated (as appropriate) so that all of the fragments (and/or fragment fingerprints) are evaluated.

At 200', a current fingerprint that is a function of an operation node and an input storage node is generated, including by generating: (1) a current artifact fingerprint associated with the artifact and (2) a current fragment fingerprint associated with the fragment, wherein the input storage node includes the artifact which in turn includes the fragment. FIG. 7 shows one example.

At 202a', the current artifact fingerprint is compared against a previously generated artifact fingerprint. For example, in FIG. 7, current fingerprint 704 is compared against output fingerprint 706.

At 204a', it is determined if the current artifact fingerprint matches the previously generated artifact fingerprint. If so, the process ends. Otherwise, the current fragment fingerprint is compared against a previously generated fragment fingerprint at 202b'. FIG. 7 illustrates an example of the "No" path at step 204a' since current fingerprint 704 and output fingerprint 706 do not match.

At 204b', it is determined if the current fragment fingerprint matches the previously generated fragment fingerprint. If so, the process ends. In FIG. 7, the first and second fragment fingerprints (718 and 720) illustrate an example of the "Yes" path at step 204b'. As a result, the operation is not rerun on or for the first and second fragments (722 and 724).

If it is determined at 204b' that the current fragment fingerprint does not match the previously generated fragment fingerprint, then at 206' a task associated with performing the operation node on the input storage node is generated, wherein the task is associated with the fragment. The third fragment fingerprint (726) in FIG. 7 illustrates an example of the "No" path at step 204b' since there is no previously generated fragment fingerprint which corresponds to the third fragment. As such, the operation is run on or for the third fragment (e.g., so that output storage node 708 in FIG. 7 can be updated with data from the third fragment).

Another benefit to artifacts and fragments is that an operation does not need to be rerun for all of the data when an operation fails (e.g., when updating an output storage node). The following figures illustrate an example of this.

Figure 9:
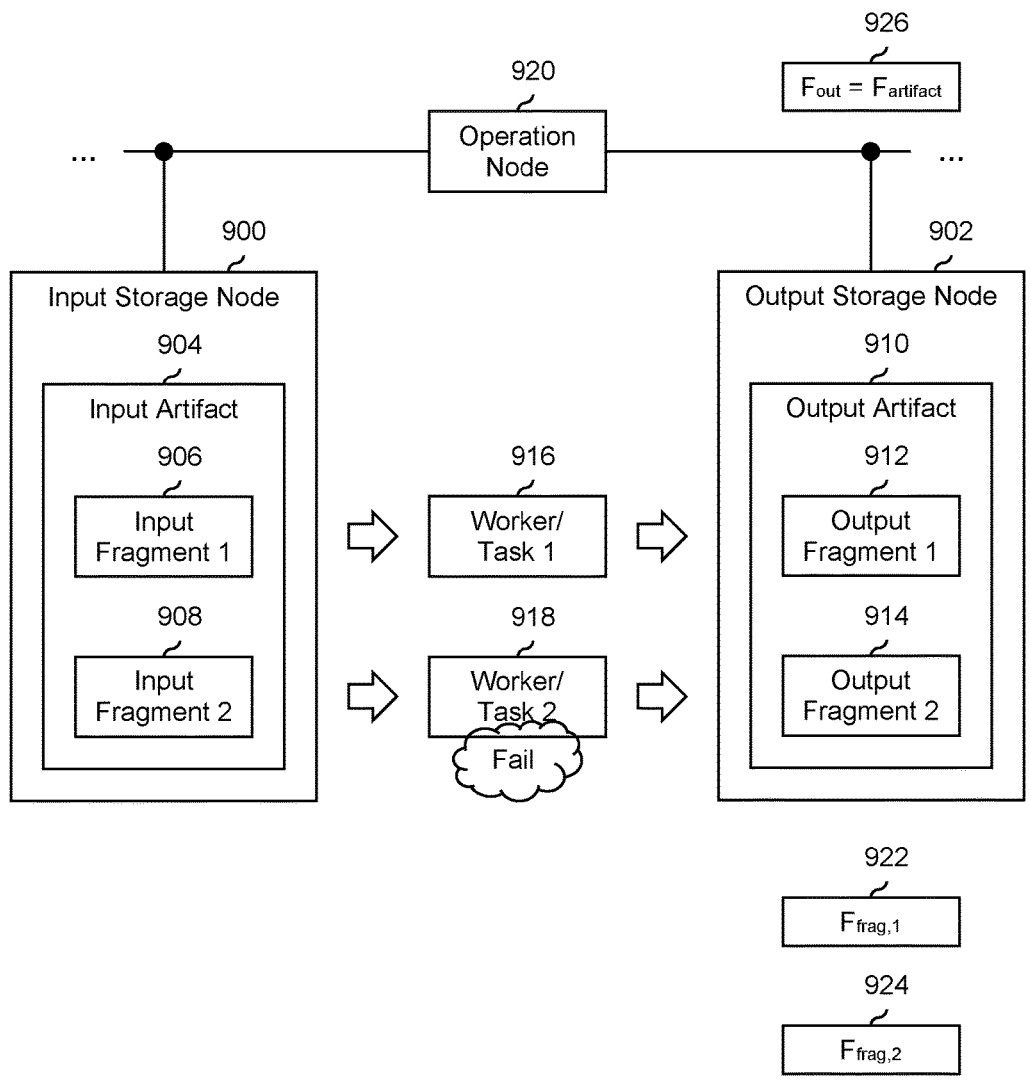
FIG. 9 is a diagram illustrating an embodiment of a datapath graph where an operation fails to update an output fragment.

FIG. 9 is a diagram illustrating an embodiment of a datapath graph where an operation fails to update an output fragment. In the example shown, data is stored on input storage node 900 and output storage node 902 in the form of artifacts and fragments. To differentiate between the artifacts and fragments on the input storage node and output storage node, the artifact and fragments on the input storage node are referred to as an input artifact (904) and input fragments (906 and 908) and the artifact and fragments on the output storage node are referred to as an output artifact (910) and output fragments (912 and 914).

In this example, to update the output storage node (902), the scheduler (not shown) generates two (sets of) tasks: one (set) which inputs the first input fragment (906) and outputs the first output fragment (912) and another (set) which inputs the second input fragment (908) and outputs the second output fragment (914). In this example, the two (sets of) tasks are performed by a first worker (916) and a second worker (918), respectively. For example, each of the (sets of) tasks may be an instance or thread of the operation associated with operation node 920.

In this example, the first task/worker (916) is successful in updating the first output fragment (912) but the second task/worker (918) fails. An error or failure message is sent to the scheduler, so the scheduler is aware that the second worker was unsuccessful at the second task. In response to the failure, the scheduler generates another task to perform the operation on the second input fragment so that the second output fragment can be updated.

In addition, the scheduler in this example does not update output fingerprint 926 (which in this case is the artifact fingerprint associated with output artifact 910) until all output fragments have been successfully updated. Output fragment fingerprints (e.g., 922 and 924) are updated after the corresponding output fragment is successfully updated (e.g., independent of the other output fragments). For example, after first task 916 successfully updates first output fragment 912, the first output fragment fingerprint (922) is updated (e.g., independent of the state of the second task 918 and/or second output fragment 914). The output fingerprint (926) is not updated at this time because all tasks have not yet completed successfully. Once the second output fragment (914) is successfully updated (e.g., at a second or later attempt), the second output fragment fingerprint (924) is updated, as is the output (artifact) fingerprint (926). This ensures that downstream operations are not initiated until all of the data in a given output storage node is ready to be propagated downstream.

The following figures more formally describe these two processes.

Figure 10:
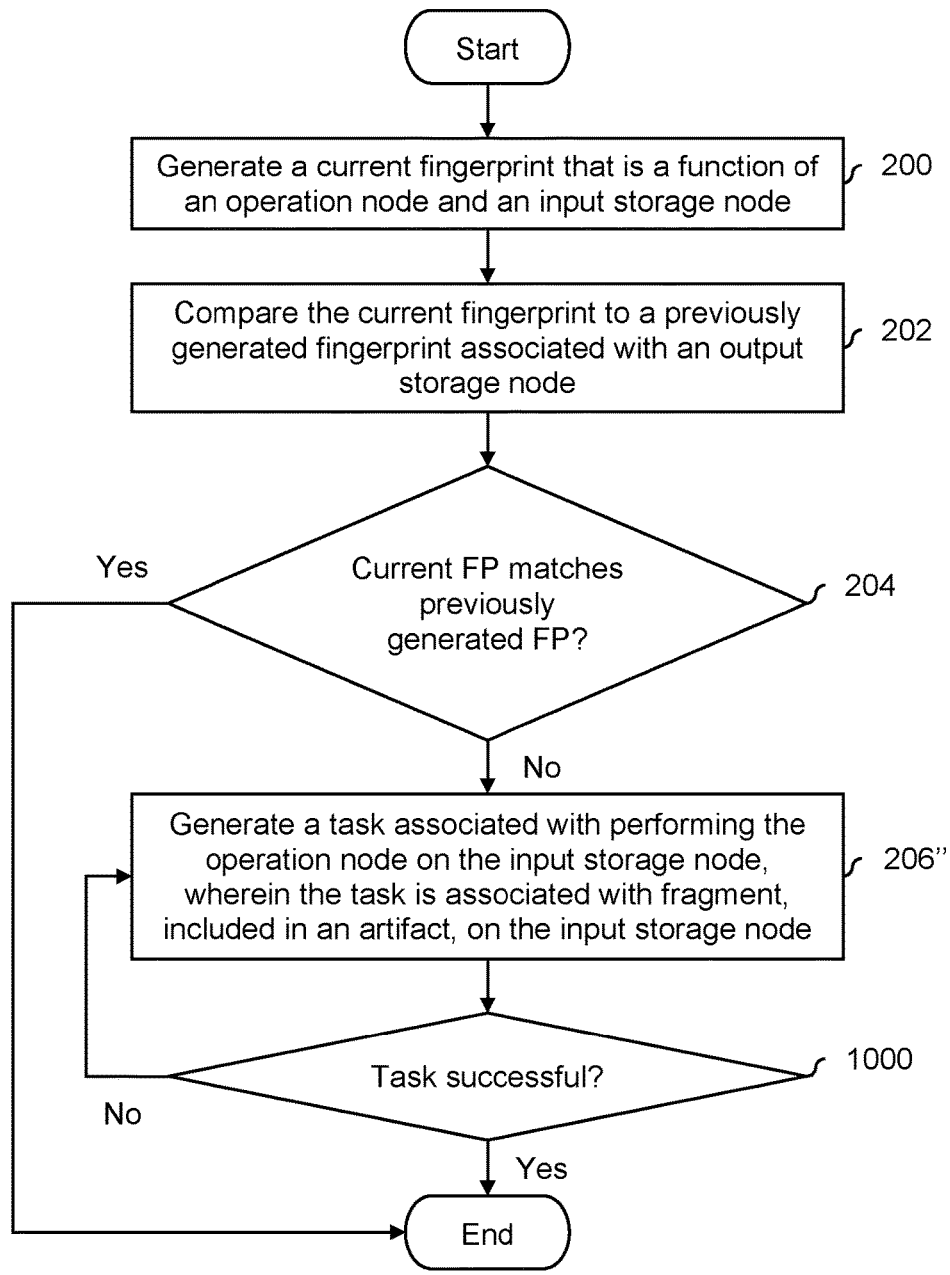
FIG. 10 is a flowchart illustrating an embodiment of a process to regenerate a task associated with performing an operation node on a fragment.

FIG. 10 is a flowchart illustrating an embodiment of a process to regenerate a task associated with performing an operation node on a fragment. FIG. 10 is similar to FIG. 2 and the same or similar reference numbers are used where appropriate.

At 200, a current fingerprint that is a function of an operation node and an input storage node is generated. At 202, the current fingerprint is compared to a previously generated fingerprint associated with an output storage node. At 204, it is determined if the current fingerprint matches a previously generated fingerprint. If so, the process ends (e.g., because the output storage node is locally up to date). Otherwise, a task associated with performing the operation node on the input storage node is generated, wherein the task is associated with a fragment, included in an artifact, on the input storage node at 206". For example, in FIG. 9, the scheduler generates a first task (916) which is directed to the first input fragment (906), as well as a second task (918) which is directed to the second input fragment (908).

At 1000, it is determined if the task is successful. For example, in FIG. 9, this decision is "Yes" for the first task (916) and is "No" for the second task (918). If the task succeeds, then the process ends (e.g., because the task does not need to be rerun). If the task fails, then the task is (re)generated at step 206". For example, in FIG. 9, the scheduler would generate another task to perform the operation on the second input fragment (908) so that the second output fragment (914) can be updated.

For brevity and to preserve readability, the example process here recites a single fragment. Naturally, steps 206" and/or 1000 may be repeated as needed to check all of the tasks (e.g., to ensure that all of the output fragments have been updated properly). For example, steps 206" and/or 1000 would be repeated as appropriate for both the first and second fragments/tasks in FIG. 9.

Figure 11:
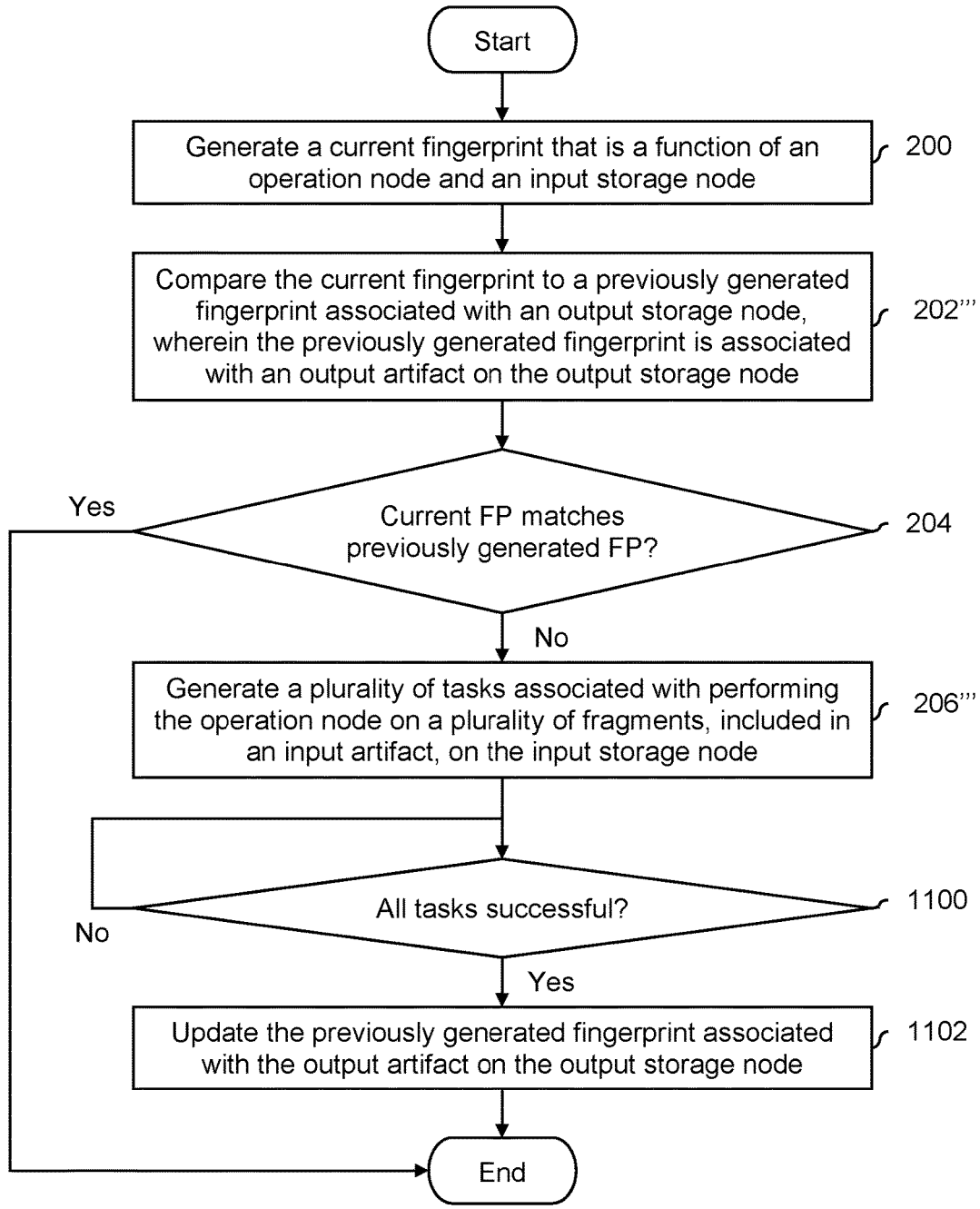
FIG. 11 is a flowchart illustrating an embodiment of a process to update a previous generated fingerprint which is associated with an output fragment.

FIG. 11 is a flowchart illustrating an embodiment of a process to update a previous generated fingerprint which is associated with an output fragment. As before, the same or similar reference numbers from FIG. 2 are used to show the same or similar steps.

At 200, a current fingerprint that is a function of an operation node and an input storage node is generated. At 202''', the current fingerprint is compared to a previously generated fingerprint associated with an output storage node, wherein the previously generated fingerprint is associated with an output artifact on the output storage node. See, for example, FIG. 9.

At 204, it is determined if the current fingerprint matches the previously generated fingerprint. If so, the process ends. If not, a plurality of tasks associated with performing the operation node on a plurality of fragments, included in an input artifact, on the input storage node are generated at 206'''. See, for example, FIG. 9.

At 1100, it is determined if all tasks are successful. If so, the previously generated fingerprint associated with the output artifact on the output storage node is updated at 1102. If not, the process waits until it is determined at 1100 that all tasks are successful.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system, comprising:
a processor; and
a memory coupled with the processor, wherein the memory is configured to provide the processor with instructions which when executed cause the processor to:
generate a current fingerprint that is a function of an operation node and an input storage node, the generating of the current fingerprint comprises to:
generate: (1) a current artifact fingerprint associated with an artifact and (2) a current fragment fingerprint associated with a fragment, wherein the input storage node includes the artifact, the artifact including the fragment, all fragments associated with the artifact storing the same particular type of data;
compare the current artifact fingerprint with a previously generated artifact fingerprint; and
in response to a determination that the current artifact fingerprint does not match the previously generated artifact fingerprint, generate a task associated with the fragment;
compare the current fingerprint to a previously generated fingerprint associated with an output storage node; and
generate a task associated with performing the operation node on the input storage node.

2. The system recited in claim 1, wherein the current fingerprint is associated with a cryptographic hash.

3. The system recited in claim 1, wherein the previously generated fingerprint is associated with a cryptographic hash.

4. The system recited in claim 1, wherein generating the current fingerprint includes combining: (1) an operation fingerprint, which is a function of the operation node, and (2) an input fingerprint, which is a function of the input storage node.

5. The system recited in claim 1, wherein:
generating the current fingerprint includes combining: (1) an input fingerprint, which is a function of the input storage node, and (2) an operation fingerprint, which is a function of the operation node; and
the input fingerprint is based at least in part on one or more of the following: a name of a group of data, a name of a file, a name of an artifact, a name of a fragment, a last time a group of data was modified, a last time a file was modified, a last time an artifact was modified, or a last time a fragment was modified.

6. The system recited in claim 1, wherein:
generating the current fingerprint includes combining: (1) an input fingerprint, which is a function of the input storage node, and (2) an operation fingerprint, which is a function of the operation node; and
the operation fingerprint is based at least in part on one or more of the following: a name of an operation, a setting associated with an operation, a path at which an operation is located, or an operation version number.

7. The system recited in claim 1, wherein:
generating the current fingerprint includes combining: (1) an input fingerprint, which is a function of the input storage node, and (2) an operation fingerprint, which is a function of the operation node;
the input fingerprint is associated with one or more logs on a source; and
the input fingerprint is based at least in part on one or more of the following: (1) a name of a script used to list names of the logs on the source or (2) a quotient function which inputs a clock and a period.

8. The system recited in claim 1, wherein the operation node includes a plurality of sub-operations.

9. The system recited in claim 1, wherein:
the task is associated with a fragment, included in an artifact, on the input storage node; and
the memory is further configured to provide the processor with instructions which when executed cause the processor to:
determine if the task is successful; and
in the event it is determined that the task is not successful, regenerate the task.

10. The system recited in claim 1, wherein:
the previously generated fingerprint is associated with an output artifact on the output storage node;
generating the task includes generating a plurality of tasks associated with performing the operation node on a plurality of fragments, included in an input artifact, on the input storage node; and
the memory is further configured to provide the processor with instructions which when executed cause the processor to:
determine if the plurality of tasks are successful; and
in the event it is determined that the plurality of tasks are successful, update the previously generated fingerprint associated with the output artifact on the output storage node.

11. A method, comprising:
generating a current fingerprint that is a function of an operation node and an input storage node, the generating of the current fingerprint comprises:
generating: (1) a current artifact fingerprint associated with an artifact and (2) a current fragment fingerprint associated with a fragment, wherein the input storage node includes the artifact, the artifact including the fragment, all fragments associated with the artifact storing the same particular type of data;
comparing the current artifact fingerprint with a previously generated artifact fingerprint; and
in response to a determination that the current artifact fingerprint does not match the previously generated artifact fingerprint, generating a task associated with the fragment;
comparing the current fingerprint to a previously generated fingerprint associated with an output storage node; and
generating a task associated with performing the operation node on the input storage node.

12. The method recited in claim 11, wherein:
generating the current fingerprint includes combining: (1) an input fingerprint, which is a function of the input storage node, and (2) an operation fingerprint, which is a function of the operation node; and
the input fingerprint is based at least in part on one or more of the following: a name of a group of data, a name of a file, a name of an artifact, a name of a fragment, a last time a group of data was modified, a last time a file was modified, a last time an artifact was modified, or a last time a fragment was modified.

13. The method recited in claim 11, wherein:
generating the current fingerprint includes combining: (1) an input fingerprint, which is a function of the input storage node, and (2) an operation fingerprint, which is a function of the operation node; and
the operation fingerprint is based at least in part on one or more of the following: a name of an operation, a setting associated with an operation, a path at which an operation is located, or an operation version number.

14. The method recited in claim 11, wherein:
generating the current fingerprint includes combining: (1) an input fingerprint, which is a function of the input storage node, and (2) an operation fingerprint, which is a function of the operation node;
the input fingerprint is associated with one or more logs on a source; and
the input fingerprint is based at least in part on one or more of the following: (1) a name of a script used to list names of the logs on the source or (2) a quotient function which inputs a clock and a period.

15. The method recited in claim 11, wherein:
the task is associated with a fragment, included in an artifact, on the input storage node; and
the memory is further configured to provide the processor with instructions which when executed cause the processor to:
determine if the task is successful; and
in the event it is determined that the task is not successful, regenerate the task.

16. The method recited in claim 11, wherein:
the previously generated fingerprint is associated with an output artifact on the output storage node;
generating the task includes generating a plurality of tasks associated with performing the operation node on a plurality of fragments, included in an input artifact, on the input storage node; and
the memory is further configured to provide the processor with instructions which when executed cause the processor to:
determine if the plurality of tasks are successful; and
in the event it is determined that the plurality of tasks are successful, update the previously generated fingerprint associated with the output artifact on the output storage node.

17. A computer program product, the computer program product being embodied in a non-transitory computer readable storage medium and comprising computer instructions for:
generating a current fingerprint that is a function of an operation node and an input storage node; node, the generating of the current fingerprint comprises:
generating: (1) a current artifact fingerprint associated with an artifact and (2) a current fragment fingerprint associated with a fragment, wherein the input storage node includes the artifact, the artifact including the fragment, all fragments associated with the artifact storing the same particular type of data;
comparing the current artifact fingerprint with a previously generated artifact fingerprint; and
in response to a determination that the current artifact fingerprint does not match the previously generated artifact fingerprint, generating a task associated with the fragment;
comparing the current fingerprint to a previously generated fingerprint associated with an output storage node; and
generating a task associated with performing the operation node on the input storage node.

\* \* \* \* \*